US010792294B2

(12) United States Patent
Buck et al.

(10) Patent No.: US 10,792,294 B2
(45) Date of Patent: Oct. 6, 2020

(54) METHODS FOR ENHANCING MUCOSAL INNATE IMMUNE RESPONSES TO AND/OR DETECTION OF PATHOGENS USING HUMAN MILK OLIGOSACCHARIDES

(71) Applicant: ABBOTT LABORATORIES, Abbott Park, IL (US)

(72) Inventors: Rachael Buck, Gahanna, OH (US); Geralyn Duska-McEwen, Columbus, OH (US); Steven Davis, Galena, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 29 days.

(21) Appl. No.: 15/302,793

(22) PCT Filed: Apr. 3, 2015

(86) PCT No.: PCT/US2015/024205
§ 371 (c)(1),
(2) Date: Oct. 7, 2016

(87) PCT Pub. No.: WO2015/157098
PCT Pub. Date: Oct. 15, 2015

(65) Prior Publication Data
US 2017/0020906 A1 Jan. 26, 2017

Related U.S. Application Data

(60) Provisional application No. 61/976,791, filed on Apr. 8, 2014.

(51) Int. Cl.
*A61K 31/7016* (2006.01)
*A61K 31/702* (2006.01)
*A23L 33/00* (2016.01)
*A23L 2/52* (2006.01)

(52) U.S. Cl.
CPC .......... *A61K 31/7016* (2013.01); *A23L 2/52* (2013.01); *A23L 33/40* (2016.08); *A61K 31/702* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,146,670 A | 11/2000 | Prieto et al. | |
| 6,540,999 B1 | 4/2003 | Harn et al. | |
| 6,863,918 B2 | 3/2005 | Bindels et al. | |
| 7,893,041 B2 | 2/2011 | Morrow et al. | |
| 8,197,872 B2 | 6/2012 | Mills et al. | |
| 9,763,970 B2* | 9/2017 | Buck ....................... | A23L 33/40 |
| 2007/0275881 A1* | 11/2007 | Morrow ................ | A61K 31/702 514/54 |
| 2011/0207659 A1 | 8/2011 | Morrow et al. | |
| 2012/0171165 A1* | 7/2012 | Buck ..................... | A61K 31/702 424/93.4 |
| 2012/0171166 A1 | 7/2012 | Chow et al. | |
| 2012/0172319 A1 | 7/2012 | Chow et al. | |
| 2012/0172327 A1* | 7/2012 | Buck ....................... | A23L 33/40 514/54 |
| 2012/0178674 A1 | 7/2012 | Stahl et al. | |
| 2012/0184503 A1 | 7/2012 | Buck | |
| 2012/0202753 A1 | 8/2012 | Morrow et al. | |
| 2012/0208782 A1 | 8/2012 | Frantz | |
| 2012/0294840 A1 | 11/2012 | Newburg et al. | |
| 2012/0308527 A1 | 12/2012 | Sprenger | |
| 2013/0012472 A1* | 1/2013 | Newburg ............. | A61K 31/726 514/54 |
| 2013/0079276 A1 | 3/2013 | Van Goudoever et al. | |
| 2013/0236423 A1 | 9/2013 | Sprenger et al. | |
| 2013/0243797 A1 | 9/2013 | Sprenger | |
| 2013/0251682 A1 | 9/2013 | Sprenger | |
| 2013/0251844 A1 | 9/2013 | Sprenger et al. | |

(Continued)

FOREIGN PATENT DOCUMENTS

| | | |
|---|---|---|
| CA | 2818011 | 6/2012 |
| CN | 101420966 A | 4/2009 |
| EP | 0975235 | 5/2006 |

(Continued)

OTHER PUBLICATIONS

Kasper, C. A., Sorg, I., Schmutz, C., Tschon, T., Wischnewski, H., Kim, M. L., & Arrieumerlou, C. (2010). Cell-cell propagation of NF-κB transcription factor and MAP kinase activation amplifies innate immunity against bacterial infection. Immunity, 33(5), 804-816 . (Year: 2010).*

Rabquer, B. J., Hou, Y., Ruth, J. H., Luo, W., Eitzman, D. T., Koch, A. E., & Amin, M. A. (2012). H-2g, a glucose analog of blood group H antigen, mediates monocyte recruitment in vitro and in vivo via IL-8/CXCL8. Open access rheumatology: research and reviews, 4, 93. (Year: 2012).*

Claud, E. C., & Walker, W. A. (2001). Hypothesis: inappropriate colonization of the premature intestine can cause neonatal necrotizing enterocolitis. The FASEB Journal, 15(8), 1398-1403. (Year: 2001).*

Netea, M. G., Simon, A., van de Veerdonk, F., Kullberg, B. J., Van der Meer, J. W., & Joosten, L. A. (2010). IL-1β processing in host defense: beyond the inflammasomes. PLoS pathogens, 6(2). (Year: 2010).*

(Continued)

*Primary Examiner* — Dale R Miller
(74) *Attorney, Agent, or Firm* — Calfee Halter & Griswold LLP (57) ABSTRACT

A method for enhancing an individual's mucosal innate immune response to pathogens is disclosed. The method includes a step of administering a nutritional composition to the individual. The nutritional composition includes about 0.05 to about 0.5 mg/mL 2'-fucosyllactose (2'-FL), about 0.05 to about 0.5 mg/mL lacto-N-neotetraose (LNnT), or a combination of both. Also disclosed is a method for enhancing an individual's mucosal innate immune detection of pathogens. The method includes a step of administering a nutritional composition to the individual. The nutritional composition includes a neutral human milk oligosaccharide.

7 Claims, 3 Drawing Sheets

(56) References Cited

U.S. PATENT DOCUMENTS

2013/0315990 A1    11/2013    Bode

FOREIGN PATENT DOCUMENTS

| | | |
|---|---|---|
| EP | 2662084 | 11/2013 |
| EP | 2217246 | 12/2014 |
| WO | 2011008087 | 1/2011 |
| WO | 2012/092156 | 7/2012 |
| WO | 2012092154 | 7/2012 |
| WO | 2012092158 | 7/2012 |
| WO | 2013032674 | 3/2013 |

OTHER PUBLICATIONS

International Search Report and Written Opinion from PCT/US2015/024205 dated Jun. 18, 2015.

Communication Pursuant to Rule 161(1) and 162 EPC from EP Application No. 15717356.8 dated Nov. 15, 2016.

Alison et al., "Experimental ulceration leads to sequential expression of spasmolytic polypeptide, intestinal trefoil factor, epidermal growth factor and transforming growth factor alpha mRNAs in rat stomach," Journal of Pathology, vol. 175, Issue 4, pp. 405-414, Apr. 1995.

Barrera et al., "Trefoil factor 3 isolated from human breast milk downregulates cytokines (IL8 and IL6) and promotes human beta defensin (hBD2 and hBD4) expression in intestinal epithelial cells HT-29," Bosn J Basic Med Sci. vol. 12, Issue 4, pp. 256-264, Nov. 2012.

Coulet et al., "Pre-clinical safety evaluation of the synthetic human milk, nature-identical, oligosaccharide 2'-O-Fucosyllactose (2'FL)," Regulatroy Toxicology and Pharmacology, vol. 68, Issue 1, pp. 59-69, Feb. 2014.

Davis et al., "Regulated airway goblet cell mucin secretion," Annu. Rev. Physiol., vol. 70, pp. 487-512 (2008).

Efstathiou et al., "Intestinal trefoil factor controls the expression of the adenomatous polyposis coli-catenin and the E-cadherin-catenin complexes in human colon carcinoma cells," Proc. Natl. Acad. Sci. USA, vol. 95, pp. 3122-3127, Mar. 1998.

Kurakevich et al., "Milk oligosaccharide sialyl($\alpha$2,3)lactose activates intestinal CD11c+ cells through TLR4," Proc. Natl. Acad. Sci. USA, vol. 110, Issue 43, pp. 17444-17449, Oct. 7, 2013.

Lane et al., "Transcriptional response of HT-29 intestinal epithelial cells to human and bovine milk oligosaccharides," British Journal of Nutrition, vol. 110, pp. 2127-2137, May 2013.

Morrow et al., "Human milk oligosaccharides are associated with protection against diarrhea in breast-fed infants," J. Pediatr., pp. 297-303 (2004).

Morrow et al., ""Human-Milk Glycans That Inhibit Pathogen Binding Protect Breast-feedingInfants against Infectious Diarrhea,"" American Society for Nutritional Sciences, vol. 135, No. 5, pp. 1304-1307, May 2005.

Neal et al., "Discovery and Validation of a New Class of Small Molecule Toll-Like Receptor 4 (TLR4) Inhibitors," PLOS one, vol. 8, Issue 6, e65779, pp. 1-10, Jun. 2013.

Newburg et al., "Innate protection conferred by fucosylated oligosaccharides of human milk against diarrhea in breastfed infants," Glycobiology, vol. 14, No. 3, pp. 253-263 (2004).

Ortega-Gonzalez et al., "Nondigestible Oligosaccharides Exert Nonprebiotic Effects on Intestinal Epithelial Cells Enhancing the Immune Response via Activation of TLR-4-NF$\kappa\beta$," Mol. Nutr. Food Res., 00, pp. 1-10 (2013).

Parker et al., "Innate immunity in the respiratory epithelium," American Journal of Respiratory Cell and Molecular Biology, vol. 45, pp. 189-201 (2011).

Tomasetto et al., "pS2/TFF1 interacts directly with the VWFC cysteine-rich domains of mucins," Gastroenterology, vol. 118, Issue 1, pp. 70-80, Jan. 2000.

Office Action from Canadian Application No. 2,942,732 dated Aug. 15, 2017.

Written Opinion from Singapore Application No. 11201608248Y dated Sep. 12, 2017.

Office Action from Canadian Patent Application No. 2942732 dated Apr. 19, 2018.

Office Action from Chinese Patent Application No. 2015800151004 dated Feb. 8, 2018.

Office Action from Canadian Patent Application No. 2942732 dated Dec. 11, 2018.

Second Office Action from Chinese Patent Application No. 201580015100A dated Oct. 18, 2018.

Examination Report from European Application No. 15717356.8 dated May 28, 2018.

Hall, et al., "Natural Killer Cells Protect Against Mucosal and Systemic Infection with the Enteric Pathogen Citrobacter Rodentium," Infection and Immunity, vol. 81, No. 2, Feb. 1, 2013, pp. 460-469 XP055477369.

Invitation to Respond to Written Opinion from Singapore Application No. 11201608248Y dated Mar. 25, 2019.

Office Action from Canadian Patent Application No. 2942732 dated Jul. 31, 2019.

Decision on Rejection from Chinese Patent Application No. 2015800151004 dated Aug. 2, 2019.

Office Action from Israeli Application No. 247465 with English Summary dated Jun. 24, 2019.

Office Action from Mexican Patent Application No. MX/a/2016/013064 dated Aug. 7, 2019.

Office Action from Canadian Patent Application No. 2942732 dated Apr. 28, 2020.

Office Action from Mexican Patent Application No. MX/a/2016/013064 dated Mar. 3, 2020.

Extended Search Report from European Application No. 20158081.8 dated May 7, 2020.

Invitation to Respond to Written Opinion from Singapore Application No. 11201608248Y dated Jun. 18, 2020.

Li, et al., "Human Milk Oligosaccharides Shorten Rotavirus-Induced Diarrhea and Modulate Piglet Mucosal Immunity and Colonic Microbiota," The ISME Journal, Feb. 13, 2014, pp. 1609-1620.

\* cited by examiner

METHODS FOR ENHANCING MUCOSAL INNATE IMMUNE RESPONSES TO AND/OR DETECTION OF PATHOGENS USING HUMAN MILK OLIGOSACCHARIDES

CROSS-REFERENCE TO RELATED APPLICATIONS

This application is the U.S. national phase entry of PCT/US2015/024205, with an international filing date of Apr. 3, 2015, which claims priority to and any benefit of U.S. Provisional Application No. 61/976,791, filed Apr. 8, 2014, the entire contents of which are incorporated herein by reference in its their entirety.

FIELD OF THE DISCLOSURE

The disclosure relates to methods for enhancing an individual's mucosal innate immune response to pathogens or an individual's mucosal innate immune detection of pathogens. Particularly, the disclosure relates to the use of nutritional compositions which include human milk oligosaccharides to enhance the individual's mucosal innate immune response to pathogens or the individual's mucosal innate immune detection of pathogens.

BACKGROUND

The immune system plays an important role in protecting individuals from pathogenic infections. Generally, the effectiveness of an immune response depends on the ability of the immune system to detect and respond to a pathogenic infection. The immune system's detection and response to pathogenic infections relies upon the expression of particular immune proteins.

SUMMARY

Disclosed herein are methods for enhancing mucosal innate immunity in an individual. Such immunity is enhanced by administering nutritional compositions including human milk oligosaccharides (HMOs) to the individual.

A method for enhancing an individual's mucosal innate immune response to pathogens is disclosed. The method includes a step of administering a nutritional composition to the individual. The nutritional composition includes about 0.05 to about 0.5 mg/mL 2'-fucosyllactose (2'-FL), about 0.05 to about 0.5 mg/mL lacto-N-neotetraose (LNnT), or a combination of both.

The present disclosure also provides a nutritional composition for use in enhancing an individual's mucosal innate immune response to pathogens wherein the nutritional composition comprises about 0.05 to about 0.5 mg/mL 2'-fucosyllactose (2'-FL), about 0.05 to about 0.5 mg/mL lacto-N-neotetraose (LNnT), or a combination of both.

The present disclosure also provides the use of a nutritional composition for the manufacture of a medicament for enhancing an individual's mucosal innate immune response to pathogens wherein the composition comprises about 0.05 to about 0.5 mg/mL 2'-FL, about 0.05 to about 0.5 mg/mL LNnT, or a combination of both.

In another aspect, a method for enhancing an individual's mucosal innate immune detection of pathogens is disclosed. The method includes a step of administering a nutritional composition to the individual. The nutritional composition includes a neutral human milk oligosaccharide.

The present disclosure also provides a nutritional composition for use in enhancing an individuals's mucosal innate immune detection of pathogens wherein the nutritional composition comprises a neutral human milk oligosaccharide.

The present disclosure also provides the use of a nutritional composition in the manufacture of a medicament for enhancing an individual's mucosal innate immune detection of pathogens wherein the composition comprises a neutral human milk oligosaccharide.

BRIEF DESCRIPTION OF THE DRAWINGS

FIG. 1 (A-D) provides graphs showing the change in RNA expression levels of genes encoding various mucosal innate immune receptor proteins, and the cytokine IL1B, in cells exposed to various treatments described in Example 1.

DETAILED DESCRIPTION

The present disclosure relates to methods for enhancing mucosal innate immunity in an individual. More specifically, such immunity is enhanced by administering nutritional compositions including human milk oligosaccharides (HMOs) to the individual.

A method for enhancing an individual's mucosal innate immune response to pathogens is disclosed. The method includes a step of administering a nutritional composition to the individual. The nutritional composition includes about 0.05 to about 0.5 mg/mL 2'-fucosyllactose (2'-FL), about 0.05 to about 0.5 mg/mL lacto-N-neotetraose (LNnT), or a combination of both.

The present disclosure also provides a nutritional composition for use in enhancing an individual's mucosal innate immune response to pathogens wherein the nutritional composition comprises about 0.05 to about 0.5 mg/mL 2'-fucosyllactose (2'-FL), about 0.05 to about 0.5 mg/mL lacto-N-neotetraose (LNnT), or a combination of both.

The present disclosure also provides the use of a nutritional composition for the manufacture of a medicament for enhancing an individual's mucosal innate immune response to pathogens wherein the composition comprises about 0.05 to about 0.5 mg/mL 2'-FL, about 0.05 to about 0.5 mg/mL LNnT, or a combination of both.

In another aspect, a method for enhancing an individual's mucosal innate immune detection of pathogens is disclosed. The method includes a step of administering a nutritional composition to the individual. The nutritional composition includes a neutral human milk oligosaccharide.

The present disclosure also provides a nutritional composition for use in enhancing an individuals's mucosal innate immune detection of pathogens wherein the nutritional composition comprises a neutral human milk oligosaccharide.

The present disclosure also provides the use of a nutritional composition in the manufacture of a medicament for enhancing an individual's mucosal innate immune detection of pathogens wherein the composition comprises a neutral human milk oligosaccharide.

In the specification, references to the method also apply to the composition where applicable, and vice versa.

Further areas of applicability of the present disclosure will become apparent from the detailed description, drawings, and claims provided hereinafter. It should be understood that the detailed description, including disclosed embodiments and drawings, are merely exemplary in nature, are only intended for purposes of illustration, and are not intended to limit the scope of the invention, its application, or use.

The term "administering," unless otherwise indicated herein, should be understood to include: a) providing the nutritional composition to an individual, b) the act of consuming the nutritional composition, and combinations thereof.

The term "nutritional composition" as used herein, unless otherwise indicated herein, refers to nutritional products in various forms including, but not limited to, liquids, solids, powders, semi-solids, semi-liquids, nutritional supplements, and any other nutritional food product known in the art. It should be understood that a nutritional composition in powder form may be reconstituted upon addition of water or another liquid to form a liquid nutritional composition prior to administration to (e.g., providing to or consumption by) an individual. As discussed below, in certain embodiments disclosed herein, the nutritional compositions comprise at least one of: a protein source, a carbohydrate source, and a fat source. The nutritional compositions disclosed herein are generally suitable for oral consumption by a human.

The term "individual," unless otherwise indicated herein, refers to a mammal, including, but not limited to, a human, a domesticated farm animal (e.g., cow, horse, pig), or a pet (e.g., dog, cat). In certain embodiments disclosed herein, the individual is a human.

The term "substantially free," unless otherwise indicated herein, means that the nutritional composition contains less than a functional amount of the ingredient. This amount will vary based on the ingredient, but is typically less than about 1%, including less than about 0.5%, including less than about 0.1%, including less than about 0.01%, including less than about 0.001%, and also including zero percent, by weight of such ingredient.

The term "human milk oligosaccharide" or "HMO," as used herein, unless otherwise indicated herein, refers to a number of complex carbohydrates found in human breast milk that can be in acidic or neutral form, and to precursors thereof. Exemplary human milk oligosaccharides include, but are not limited to, lacto-N-neotetraose and 2'-fucosyllactose. Exemplary human milk oligosaccharide precursors include, but are not limited to, fucose. As a natural constituent of human breast milk, HMOs are largely believed to be benign in character. The term "human milk oligosaccharide" or "HMO" should be understood to include "neutral HMOs," e.g., fucosylated oligosaccharides and N-acetylated oligosaccharides.

The nutritional compositions used in the methods disclosed herein may comprise, consist of, or consist essentially of the elements of the products as described herein, as well as any additional or optional element described herein or otherwise useful in nutritional product applications. For example, as used herein, the term "comprising" is intended to mean that a composition or method includes the recited features, but that other features are not excluded, and the term "consisting of" is intended to mean that a composition or method includes only the recited features.

Unless otherwise indicated herein, concentrations of HMOs provided are the concentrations of the HMOs in the nutritional composition as administered to an individual. The concentration is the final concentration after dilution of a concentrated liquid or mixing of a powder with a liquid to form a liquid nutritional composition appropriate for administration to an individual.

As previously discussed, disclosed herein are methods for enhancing mucosal innate immunity in an individual. In some embodiments, mucosal innate immunity enhancement involves enhancing one or both of the individual's mucosal innate immune response to pathogens and the individual's mucosal innate immune detection of pathogens. The enhancement is achieved by administering a nutritional composition including one or more HMOs to the individual, as described in further detail herein.

Generally, the HMOs included in the nutritional compositions used in the methods disclosed herein may include any of a number of HMOs known in the art. Such HMOs include the oligosaccharides found in human breast milk. In certain embodiments, suitable HMOs for use in the nutritional compositions used in the disclosed methods include any neutral HMO, including HMO precursors. Specific non-limiting examples of neutral HMOs and precursors include D-glucose (Glc); D-galactose (Gal); L-fucose (Fuc); Lacto-N-Tetraose, Lacto-N-Neotetraose, Lacto-N-Hexaose, Para-Lacto-N-Hexaose, Lacto-N-Neohexaose, Para-Lacto-N-Neohexaose; fucosyl oligosaccharides (i.e., Lacto-N-fucopentaose I; Lacto-N-fucopentaose II; 2'-Fucosyllactose; 3'-Fucosyllactose; Lacto-N-fucopentaose III; Lacto-N-difucohexaose I; and Lactodifucotetraose). These HMOs are described more fully in U.S. Patent Application Publication No. 2009/0098240, which is hereby incorporated by reference herein in its entirety. In certain embodiments, the HMOs used in the nutritional compositions used in the disclosed methods include at least one of the following HMOs: lacto-N-neotetraose (LNnT), and 2'-fucosyllactose (2'-FL).

In certain embodiments, the nutritional compositions may include or exclude any HMO or combination of HMOs disclosed herein. In particular embodiments, when the nutritional composition includes LNnT or 2'-FL, the nutritional composition is substantially free of other HMOs. In other embodiments, the nutritional composition includes both LNnT and 2'-FL. Also, in particular embodiments, the nutritional composition is substantially free of any HMO other than LNnT or 2'-FL. In other words, in such embodiments, the nutritional composition can: (1) contain LNnT but is substantially free of all other HMOs, (2) contain 2'-FL but is substantially free of all other HMOs, or (3) can contain LNnT and 2'-FL but is substantially free of all other HMOs.

In some embodiments, the HMOs are present in the nutritional compositions in total amounts of HMO (i.e., all HMOs that are present) in the nutritional composition (mg of total HMO per mL of nutritional composition, as administered) of at least about 0.001 mg/mL, including at least about 0.01 mg/mL, including from about 0.001 mg/mL to about 20 mg/mL, including from about 0.01 mg/mL to about 20 mg/mL, including from about 0.001 mg/mL to about 10 mg/mL, including from about 0.01 mg/mL to about 10 mg/mL, including from about 0.001 mg/mL to about 5 mg/mL, including from about 0.01 mg/mL to about 5 mg/mL, including from about 0.001 mg/mL to about 1 mg/mL, including from about 0.001 mg/mL to about 0.23 mg/mL, including from about 0.01 mg/mL to about 0.23 mg/mL of total HMO in the nutritional composition. Typically, the amount of total HMO in the nutritional composition will depend on the specific HMO or HMOs present and the amounts of other components in the nutritional composition.

In some embodiments where 2'-FL is present in the nutritional compositions, and the nutritional compositions are used in a method to enhance mucosal innate immune detection of pathogens, it is present in an amount of from about 0.001 mg/mL to about 2.5 mg/mL, including from about 0.01 mg/mL to about 2.5 mg/mL. In some embodiments, 2'-FL is present in the nutritional compositions at concentrations of less than 1 mg/mL, including less than 0.5 mg/mL, including from about 0.05 to about 0.5 mg/mL, and including about 0.05 to about 0.25 mg/mL.

In other embodiments where 2'-FL is present in the nutritional compositions, and the nutritional compositions are used in a method to enhance a mucosal innate immune response to pathogens, it is present at concentrations of less than 1 mg/mL, including less than 0.5 mg/mL, including from about 0.05 to about 0.5 mg/mL, and including about 0.05 to about 0.25 mg/mL.

In some embodiments, where LNnT is present in the nutritional composition, it is present in an amount of from about 0.001 mg/mL to less than about 0.2 mg/mL, including from about 0.01 mg/mL to less than about 0.2 mg/mL, and also greater than about 0.32 mg/mL, including about 2 mg/mL. In some embodiments, LNnT is present in the nutritional composition at concentrations of less than 1 mg/mL, including less than 0.5 mg/mL, including about 0.05 to about 0.5 mg/mL, and including about 0.25 mg/mL to about 0.5 mg/mL.

In some embodiments, the nutritional compositions may contain any combination of any of the HMOs disclosed herein. The HMOs may be present in any combination of individual HMO concentrations or total HMO concentrations disclosed herein. Thus, in some embodiments, the nutritional compositions include both LNnT and 2'-FL, each at a concentration of less than 1 mg/mL. In a particular embodiment, the nutritional composition includes LNnT and 2'-FL, each at a concentration of about 0.05 to about 0.5 mg/mL.

In certain embodiments, the HMOs are synthetic, e.g., produced via microbial fermentation, enzymatic processes, chemical synthesis, or combinations thereof.

Applicants have unexpectedly discovered that particular HMOs (e.g., LNnT and 2'-FL) can be used to enhance mucosal innate immunity in an individual. Surprisingly, these HMOs can be used to enhance one or more of the individual's mucosal innate immune response to pathogens and the mucosal innate immune detection of pathogens. Applicants have identified methods which include administering nutritional compositions containing one or more HMOs, including those HMOs described above, to enhance an individual's mucosal innate immunity.

In some embodiments, an individual's mucosal innate immune response to pathogens is enhanced by administering a nutritional composition including one or both of LNnT and 2'-FL. In certain of these embodiments, where present, 2'-FL is present in a concentration of about 0.05 to about 0.5 mg/mL, and, where present, LNnT is present in a concentration of about 0.05 to about 0.5 mg/mL.

Without being bound by theory, it is believed that the methods disclosed herein (i.e., administration of nutritional compositions comprising the HMOs described above) enhance the mucosal innate immune response to pathogens in an individual by increasing the expression of immune proteins. In some embodiments, the administration of the nutritional composition to an individual enhances the individual's mucosal innate immune response to pathogens by increasing the expression of: one or more mucosal innate immune receptors, one or more cytokines, one or more mucosal innate immune defense proteins, or combinations thereof. In specific embodiments, the mucosal innate immune receptors that are increased in expression are one or more of Toll-like receptor 3 (TLR3), Toll-like receptor 4 (TLR4), and Chemokine receptor 2 (CCR2). In specific embodiments, expression of the cytokine Interleukin-1 beta (IL1B) is increased. In a particularly specific embodiment, the mucosal innate immune defense protein is Mucin 2 (MUC2). Without being bound by theory, it is believed that increased expression of mucosal innate immune receptors and cytokines can enhance the mucosal innate immune response to pathogens by enhancing innate defenses and/or improving mucosal immune function. Increased expression of the receptors is believed to lead to increased expression of mucosal innate immune defense proteins with antimicrobial activity, including MUC2, which leads to an enhanced antimicrobial response.

In some embodiments, an individual's mucosal innate immune detection of pathogens is enhanced by administering a nutritional composition including a neutral HMO. The neutral HMO can be any neutral HMO, including any of the neutral HMOs listed above. In a particularly specific embodiment, the neutral HMO used to enhance the individual's mucosal innate immune detection of pathogens is 2'-FL. In those embodiments where 2'-FL is the neutral HMO, 2'-FL may be present in the nutritional composition in any concentration disclosed herein. In a specific embodiment, 2'-FL is present in the nutritional composition at a concentration of less than 1 mg/mL. In another particularly specific embodiment, the neutral HMO used to enhance the individual's mucosal innate immune detection of pathogens is LNnT. In those embodiments where LNnT is the neutral HMO, LNnT may be present in the nutritional composition in any concentration disclosed herein. In a specific embodiment, LNnT is present in the nutritional composition at a concentration of less than 1 mg/mL.

Without being bound by theory, it is believed that the methods disclosed herein (i.e., administration of nutritional compositions comprising the HMOs described above) enhance mucosal innate immune detection of pathogens in an individual by increasing the expression of immune proteins. In some embodiments, the administration of the nutritional composition to an individual enhances the individual's mucosal innate immune detection by increasing the expression of one or more mucosal innate immune receptors and/or by increasing the expression of one or more cytokines. In specific embodiments, the mucosal innate immune receptors are one or more of TLR3, TLR4, and CCR2. In specific embodiments, the cytokine is IL1B. Without being bound by theory, it is believed that increased expression of these receptors and/or IL1B enhances mucosal innate immune detection of pathogens by increasing the individual's immune surveillance for pathogens.

In some embodiments, the methods disclosed herein involve administering a nutritional composition that has select combinations of HMOs. The combination of HMOs may be any combination of HMOs disclosed herein or otherwise known in the art, so long as the combination is effective at increasing mucosal innate immunity. In some embodiments, the methods involve administering a nutritional composition that contains one but not both of 2'-FL and LNnT. In other embodiments, the methods involve administering a nutritional composition which is substantially free of any HMO other than 2'-FL or LNnT.

In some embodiments, the methods involve administering nutritional compositions which include LNnT and/or 2'-FL each at concentrations below about 0.5 mg/mL. In some embodiments, the methods involve administering a nutritional composition containing about 0.05 to about 0.25 mg/mL of 2'-FL and/or about 0.25 mg/mL to about 0.5 mg/mL of LNnT.

In some embodiments, the methods disclosed herein involve administering a nutritional composition which includes at least one of: a protein source, a carbohydrate source, and a fat source. It should be understood that a protein source includes one or more than one source of protein, a carbohydrate source includes one or more than one source of carbohydrate, and a fat source includes one or more than one source of fat. As well, certain sources may provide more than one macronutrient (e.g., both fat and protein).

In those embodiments where the nutritional composition includes a protein source, the protein source can include, but is not limited to, one or more of whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, nonfat dry milk, condensed skim milk, soy protein concentrates, soy protein isolates, soy protein hydrolysates, pea protein concentrates, pea protein isolates, pea protein hydrolysates, collagen proteins, potato proteins, rice proteins, fungal proteins, proteins expressed by microorganisms, and combinations thereof.

In those embodiments where the nutritional composition includes a carbohydrate source, the carbohydrate source can include, but is not limited to, one or more of maltodextrin; hydrolyzed or modified starch or cornstarch; glucose polymers; corn syrup; corn syrup solids; rice-derived carbohydrates; high fructose corn syrup; honey; sugar alcohols, such as maltitol, erythritol, sorbitol, glycerine; sucrose; glucose; fructose; lactose; isomaltulose, sucromalt, pullulan, potato starch, and other slowly-digested carbohydrates; oligosaccharides such as fructo-oligosaccharides or galactooligosaccharides; dietary fibers including, but not limited to, oat fiber, inulin, polydextrose, soy fiber, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low and high methoxy pectin, cereal beta-glucans, carrageenan and psyllium, soluble dietary fibers such as digestion resistant maltodextrins, resistant modified food starches, other resistant starches; soluble and insoluble fibers derived from fruits or vegetables; and combinations thereof.

In those embodiments where the nutritional composition includes a fat source, the fat source can include, but is not limited to, one or more of coconut oil, fractionated coconut oil, soy oil, corn oil, olive oil, safflower oil, high oleic safflower oil, medium chain triglyceride oil, high gamma linolenic safflower oil, sunflower oil, high oleic sunflower oil, palm oil, palm kernel oil, palm olein, canola oil, marine oils, algal oils, cottonseed oils, interesterified oils, transesterified oils, monoglycerides, diglycerides, free fatty acids and combinations thereof. The nutritional composition may also include any combination of protein, carbohydrate, and fat sources described herein.

Generally, the methods disclosed herein involve administering the nutritional composition in any manner that allows for enhancement of a mucosal innate immune response to pathogens and/or enhancement of mucosal innate immune detection of pathogens.

In some embodiments, the methods disclosed herein involve orally administering the nutritional composition to an individual. Oral administration, as defined herein, includes any form of administration in which the nutritional composition passes through the esophagus of the individual. For example, oral administration typically refers to oral consumption, but may also include nasogastric intubation, in which a tube is run from the nose to the stomach of the individual to administer the composition. Particularly suitable oral formulations include nutritional beverages, powders, bars, gels, or sachets sprinkled on food or dissolved in water.

Generally, the nutritional compositions used in the methods disclosed herein can be in any form that can be effectively provided to an individual to enhance the individual's mucosal innate immunity. In particular embodiments, the nutritional composition is in the form of one or more of the following: liquid and powdered dietary supplements, liquid and powdered human milk fortifiers, liquid and powdered preterm infant formulas, liquid and powdered infant formulas, liquid and powdered elemental and semi-elemental formulas, liquid and powdered pediatric formulas, liquid and powdered toddler formulas, liquid and powdered follow-on formulas, and liquid, powdered and solid adult nutritional formulas In other embodiments, the methods involve topically administering the HMO (e.g., 2'-FL, LNnT, or both) to an individual. Topical administration involves applying a composition including the HMO(s) to an area where sufficient absorption will occur (e.g., a mucosal surface such as the nasal cavity, lung cavity, vaginal cavity, eyes or the skin). Common forms of topical administration include, but are not limited to, drops, sprays, creams, ointments, lotions, pastes, jellies, aerosols, and bath oils.

The nutritional compositions administered in the methods disclosed herein can generally be made by methods known in the art. Such methods are disclosed in various patent application publications and patents including U.S. Patent Publication 2012/0172307 A1, U.S. Pat. Nos. 6,365,218, 6,306,908, and U.S. Patent Publication 2003/0118703 A1, each of which is incorporated herein by reference for the disclosure of such methods.

In one suitable manufacturing process, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MN slurry is formed by adding with heated agitation to water minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., HMOs, fructooligosaccharide, sucrose, corn syrup, etc.). The PIW slurry is then formed by mixing with heat and agitating the remaining protein, if any. The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

In some embodiments, the methods disclosed herein are directed towards individuals with a particular disposition or susceptibility to pathogenic infections or to an individual who may already exhibit symptoms of infection. Such individuals can be qualified as being "in need of" treatment. In particular embodiments, individuals "in need of" treatment have one or more of an enteric infection, inflammatory bowel disease, irritable bowel syndrome, necrotizing enterocolitis, colitis, bowel obstruction, chronic stress, other gastrointestinal diseases, antibiotic therapy, radiation therapy, chemotherapy, surgery, other treatments or therapies; and dehydration.

Individuals with enhanced mucosal innate immunity can be identified by any method known in the art. In some embodiments, the enhancement of an individual's mucosal innate immune response to pathogens is identified by the individual having increased expression of one or more of innate immune receptors, select cytokines, and innate immune defense proteins. The innate immune receptors are one or more of TLR3, TLR4, and CCR2. IL1B is an example of a select cytokine. The innate immune defense protein is preferably MUC2.

In some embodiments, the enhancement of an individual's mucosal innate immune detection of pathogens is identified by the individual having increased expression of one or more of innate immune receptors and select cytokines. As discussed above, the innate immune receptors are one or more of TLR3, TLR4, and CCR2. IL1B is an example of a select cytokine.

In some embodiments, the enhancement of the individual's mucosal innate immune detection of pathogens, mucosal innate immune response to pathogens, or both, is identified by measuring changes in expression of one or more of innate immune receptors, select cytokines, and innate immune defense proteins in a model organism following administration of a nutritional composition disclosed herein to the model organism. The model organism can be any known model organism for measuring these properties. In some embodiments, the model organism is a pig, and, in particular, a piglet.

EXAMPLES

The following examples illustrate specific and exemplary embodiments, features, or both, of the methods disclosed herein. While the examples describe the use of specific HMOs described herein, it should be recognized that the protocols described hereinafter can be used to test the ability of any HMO, and nutritional compositions made therefrom, to enhance mucosal innate immunity in an individual. The examples are provided solely for the purpose of illustration and should not be construed as limitations on the present disclosure.

Example 1

HMOs Increase the Expression of Mucosal Innate Immune Receptors and Select Cytokines In this study, cells exposed to 2'-FL or LNnT, alone, exhibited increased expression of mucosal innate immune receptors in an in vitro exposure assay.

The ability of HMOs to increase expression of mucosal innate immune receptors and cytokines was tested by exposing LS174T human colorectal cancer cells, which are a model of human intestinal goblet cells, to either of the HMOs, 2'-FL or LNnT. The LS174T cells were obtained from the American Type Culture Collection (ATCC). LS174T cells were maintained in minimum essential medium supplemented with 10% Fetalplex, 1.5 g/L of $Na_2CO_3$, 10 ml/L penicillin G-streptomycin solution at 37° C. in 5% $CO_2$. Cells were plated at $0.2\times10^5$ cells/ml/well in 24-well plates and allowed to attach for 24-30 hours. Solutions containing each HMO were prepared by resuspending lyophilized HMO in cell culture grade water to a 10% solution and filter-sterilizing before diluting to the appropriate level in culture media. A solution free of carbohydrates (i.e., fresh medium alone, Control) was also prepared using the same procedure. After preparation of the HMO-containing solutions, the LS174T cell cultures were rinsed with 1×HBSS and then incubated in 0.5 ml of fresh medium alone (Control) or containing 0.1 mg/mL or 1 mg/mL of 2'-FL (2FL), LNnT (LNnT), fucose (FUCOSE), or lactose (LAC) for 48 hours. Cells were harvested at the end of incubation with 1 ml of TRIzol to obtain RNA samples.

RNA expression levels of the genes for the mucosal innate immune receptor proteins TLR3, TLR4, CCR2 and the cytokine IL1B were determined by quantitative reverse transcriptase polymerase chain reaction (qRT-PCR) of RNA samples from the cells. Fold change (Fold induction) in the RNA expression levels of the genes for the receptor proteins and the cytokine was normalized based on the change in GUSB transcript expression. Reported fold changes are the mean+/−3 SEM. Treatments with statistically significant differences in fold expression (P<0.05) are reported with different letters above the bars.

As shown in FIGS. 1A-1D, cells exposed to 2'-FL at a concentration of 1 mg/mL exhibited a statistically significant fold change in RNA expression in each of the four genes relative to Control. Cells exposed to 2'-FL at a concentration of 0.1 mg/mL exhibited a statistically significant fold change in RNA expression of TLR3, TLR4, and CCR2 relative to Control. Surprisingly, these genes had a greater increase in expression in response to the 0.1 mg/mL 2'-FL treatment than the 1 mg/mL 2'-FL treatment. Particularly surprising was the result that, of the HMOs tested, only 2'-FL showed an increase in expression at the lower level of 0.1 mg/mL for more than one gene (more specifically, three genes).

Also shown in FIGS. 1A-1D, exposure of the cells to 1 mg/mL of LNnT produced a significant change in expression of all four genes relative to Control. CCR2 expression was also significantly enhanced at an LNnT concentration of 0.1 mg/mL.

Example 2

HMOs Increase the Expression of Mucosal Innate Immune Defense Proteins

In this study, cells exposed to 2'-FL, alone, exhibited increased expression of the mucosal innate immune defense protein, MUC2, in an in vitro exposure assay.

Figure 1A:
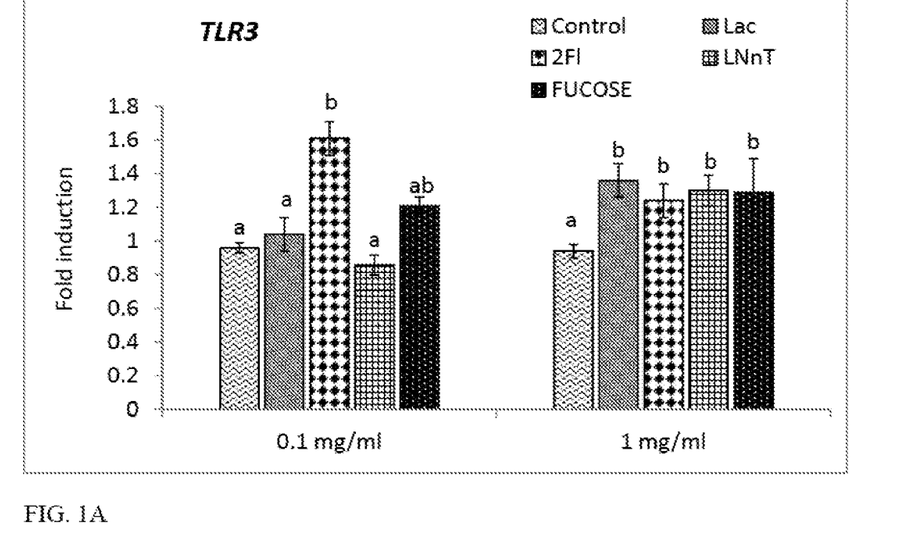
Figure 1B:
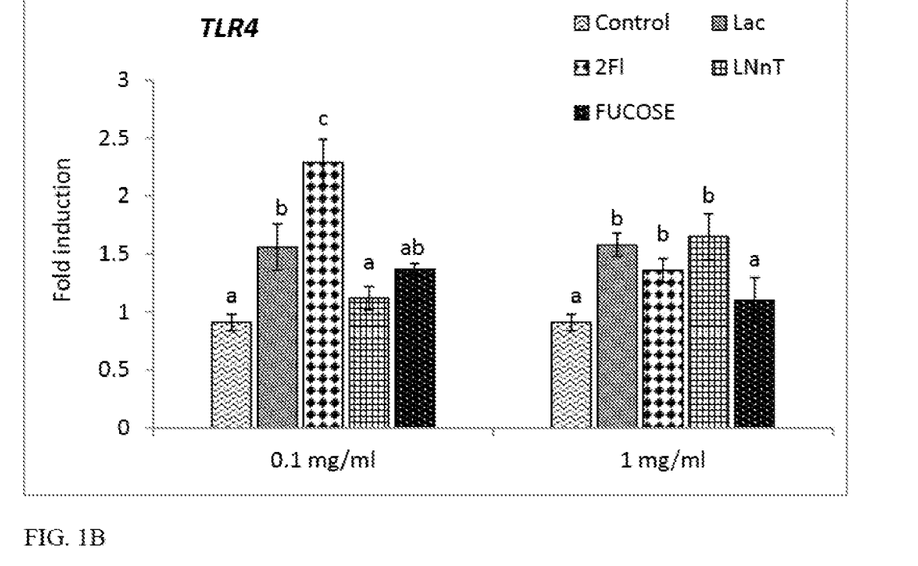
Figure 1C:
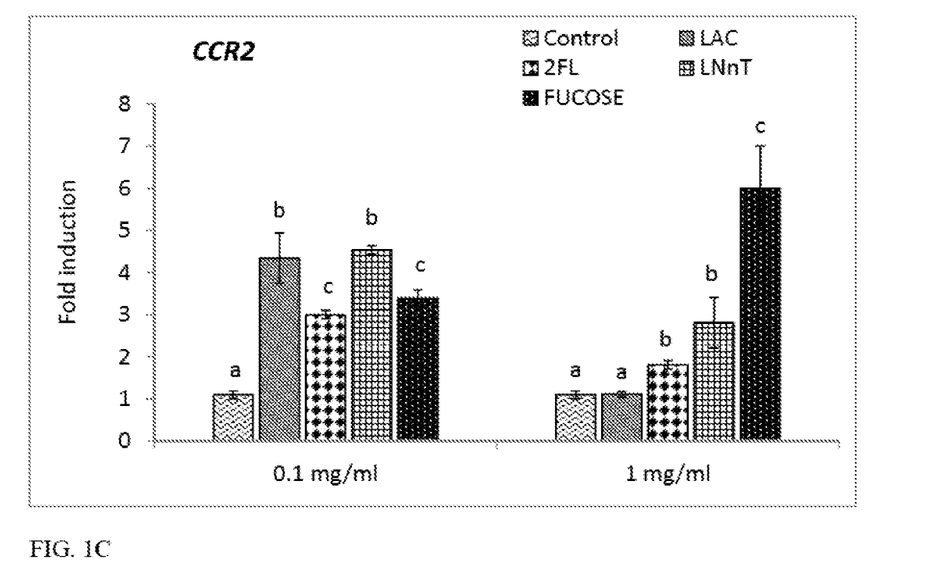
Figure 1D:
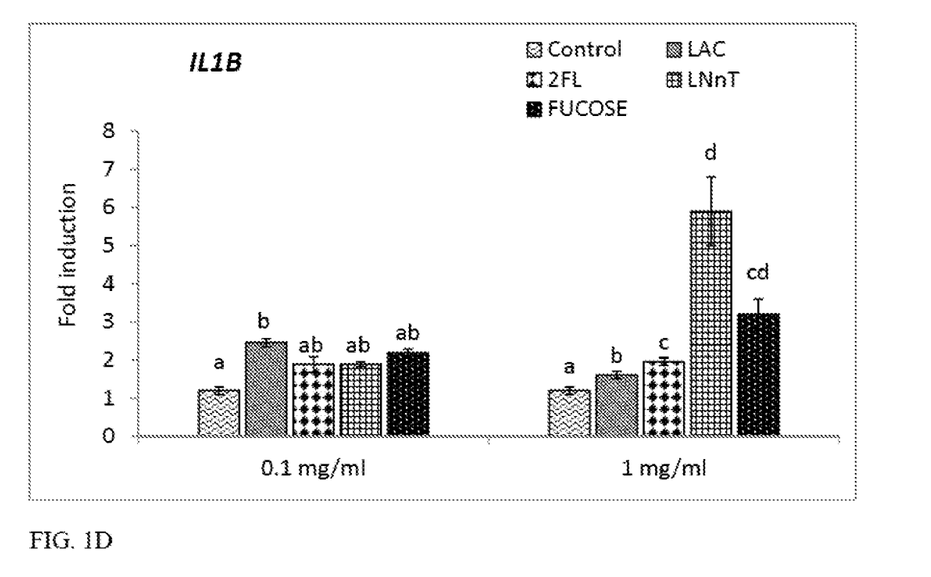
Figure 2:
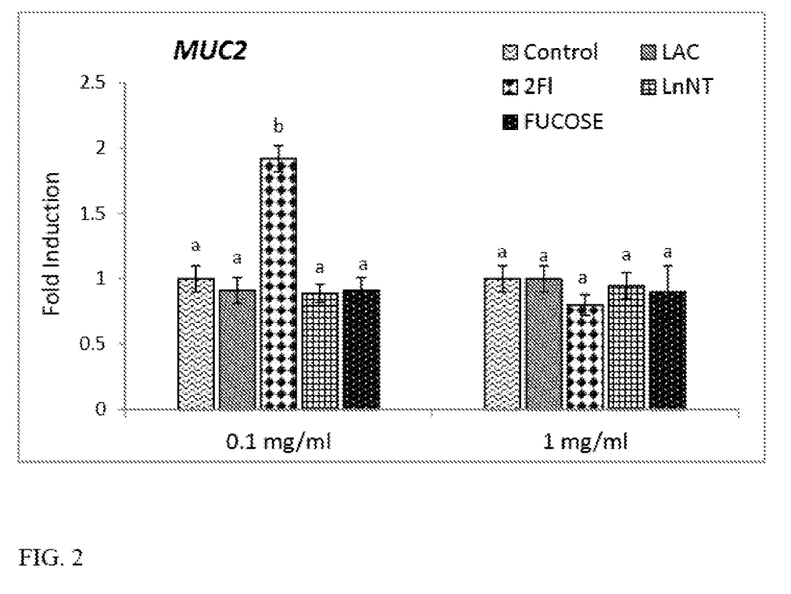
FIG. 2 is a graph showing the change in the RNA expression level of the gene encoding the mucosal innate immune defense protein, MUC2, in cells exposed to various treatments described in Example 2.

Experiments were carried out as described in Example 1, except the qRT-PCR assay was targeted to measure the RNA expression of the gene coding for MUC2. As shown in FIG. 2, cells exposed to 0.1 mg/mL of 2'-FL exhibited a significant increase in MUC2 gene expression.

Unless otherwise indicated herein, all sub-embodiments and optional embodiments are respective sub-embodiments and optional embodiments to all embodiments described herein. While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative compositions or formulations, and illustrative examples shown and described. Accordingly, departures may be made from such details without departing from the spirit or scope of the applicant's general disclosure herein.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

As used in the description of the invention and the appended claims, the singular forms "a," "an," and "the" are intended to include the plural forms as well, unless the context clearly indicates otherwise.

The invention claimed is:

1. A method for stimulating expression of one or more of innate immune receptors and innate immune cytokines comprising administering a nutritional composition comprising about 0.05 mg/mL to about 0.5 mg/mL 2'-fucosyllactose (2'-FL), to an individual in need thereof, wherein the innate immune receptors are selected from the group consisting of TLR3, TLR4, and CCR2, and wherein the innate immune cytokine is IL1B, wherein stimulating expression of one or more of innate immune receptors and innate immune cytokines increases the individual's mucosal innate immune detection of pathogens.

2. The method of claim 1, wherein the nutritional composition is a nutritional composition selected from liquid and powdered dietary supplements, liquid and powdered human milk fortifiers, liquid and powdered preterm infant formulas, liquid and powdered infant formulas, liquid and powdered elemental and semi-elemental formulas, liquid and powdered pediatric formulas, liquid and powdered toddler formulas, liquid and powdered follow-on formulas, and liquid, powdered and solid adult nutritional formulas.

3. The method of claim 1, wherein the individual to whom the nutritional composition is administered has one or more of an enteric infection, inflammatory bowel disease, irritable bowel syndrome, necrotizing enterocolitis, colitis, bowel obstruction, chronic stress, other gastrointestinal diseases, antibiotic therapy, radiation therapy, chemotherapy, surgery, other treatments or therapies; and dehydration.

4. The method of claim 1, wherein the nutritional composition is a nutritional composition selected from liquid and powdered human milk fortifiers.

5. The method of claim 1, wherein the nutritional composition is a nutritional composition selected from liquid and powdered preterm infant formulas.

6. The method of claim 1, wherein the nutritional composition is a nutritional composition selected from liquid and powdered pediatric formulas.

7. The method of claim 1, wherein the nutritional composition is a nutritional composition selected from liquid, powdered and solid adult nutritional formulas.

* * * * *